United States Patent
Finley

(10) Patent No.: US 9,549,768 B2
(45) Date of Patent: Jan. 24, 2017

(54) MEDICAL IMPLANT SYSTEM FOR SECURING BONE FRAGMENTS

(71) Applicant: Biomet Manufacturing, LLC, Warsaw, IN (US)

(72) Inventor: Adam Finley, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 525 days.

(21) Appl. No.: 14/255,619

(22) Filed: Apr. 17, 2014

(65) Prior Publication Data

US 2015/0297271 A1  Oct. 22, 2015

(51) Int. Cl.
*A61B 17/80* (2006.01)
*A61B 17/82* (2006.01)

(52) U.S. Cl.
CPC ........... *A61B 17/8004* (2013.01); *A61B 17/80* (2013.01); *A61B 17/8061* (2013.01); *A61B 17/82* (2013.01)

(58) Field of Classification Search
CPC . A61B 17/80; A61B 17/8004; A61B 17/8023; A61B 17/8028; A61B 17/8033; A61B 17/8038; A61B 17/8042; A61B 17/8047; A61B 17/8052; A61B 17/8057; A61B 17/8061; A61B 17/8066; A61B 17/8071; A61B 17/8076; A61B 17/82; A61B 17/823; A61B 17/826
See application file for complete search history.

(56) References Cited

U.S. PATENT DOCUMENTS

| | | | |
|---|---|---|---|
| 4,889,110 A | 12/1989 | Galline et al. | |
| 5,190,545 A * | 3/1993 | Corsi | A61B 17/82 606/309 |
| 5,324,291 A | 6/1994 | Ries et al. | |
| 5,415,658 A * | 5/1995 | Kilpela | A61B 17/8861 606/297 |
| 5,741,259 A * | 4/1998 | Chan | A61B 17/842 606/103 |
| 5,797,915 A | 8/1998 | Pierson, III et al. | |
| 5,797,916 A * | 8/1998 | McDowell | A61B 17/842 606/286 |
| 5,908,421 A * | 6/1999 | Beger | A61B 17/82 606/151 |
| 6,066,141 A * | 5/2000 | Dall | A61B 17/82 606/281 |
| 6,338,734 B1 * | 1/2002 | Burke | A61B 17/74 606/280 |
| 6,648,903 B1 | 11/2003 | Pierson, III | |
| 7,207,993 B1 * | 4/2007 | Baldwin | A61B 17/74 606/300 |
| 7,601,165 B2 | 10/2009 | Stone | |
| 7,611,513 B2 | 11/2009 | Deloge et al. | |

(Continued)

*Primary Examiner* — Christian Sevilla
*Assistant Examiner* — Eric S Gibson
(74) *Attorney, Agent, or Firm* — Schwegman Lundberg & Woessner, P.A.

(57) ABSTRACT

A medical implant system includes a bone plate including a groove, a dynamic connector positioned within said groove of said bone plate, and an elongate flexible member. The dynamic connector includes a tip end having a through-hole, a tension spring having an end coupled to the tip end, and a head coupled to an opposing end of the tension spring. The elongate flexible member extends through the through-hole of said tip end and is secured to the head.

21 Claims, 3 Drawing Sheets

(56) References Cited

U.S. PATENT DOCUMENTS

| | | | |
|---|---|---|---|
| 7,731,718 B2 | 6/2010 | Schwammberger et al. | |
| 8,142,434 B2* | 3/2012 | Bluechel | A61B 17/8061 606/280 |
| 8,226,693 B2 | 7/2012 | Reimels et al. | |
| 8,231,626 B2 | 7/2012 | Hulliger et al. | |
| 8,303,591 B1 | 11/2012 | Foerster | |
| 8,343,155 B2 | 1/2013 | Fisher et al. | |
| 8,403,930 B2 | 3/2013 | Chico Roca | |
| 8,574,235 B2* | 11/2013 | Stone | A61B 17/0401 606/74 |
| 2004/0087954 A1* | 5/2004 | Allen | A61B 17/82 606/74 |
| 2004/0225291 A1 | 11/2004 | Schwammberger et al. | |
| 2006/0058795 A1* | 3/2006 | Boyd | A61B 17/82 606/281 |
| 2006/0135958 A1* | 6/2006 | Marissen | A61B 17/823 606/74 |
| 2008/0234679 A1* | 9/2008 | Sarin | A61B 17/74 606/70 |
| 2009/0312758 A1* | 12/2009 | Petit | A61B 17/74 606/60 |
| 2010/0211071 A1 | 8/2010 | Lettmann et al. | |
| 2010/0211078 A9 | 8/2010 | Riemer et al. | |
| 2010/0234896 A1* | 9/2010 | Lorenz | A61B 17/74 606/286 |
| 2011/0137314 A1 | 6/2011 | Kuster et al. | |
| 2012/0083848 A1* | 4/2012 | Gonzalez-Hernandez | A61B 17/0401 606/281 |
| 2012/0290017 A1* | 11/2012 | Haidukewych | A61B 17/68 606/324 |
| 2013/0131738 A1* | 5/2013 | Powell | A61B 17/84 606/324 |
| 2013/0138105 A1 | 5/2013 | Park | |
| 2013/0274748 A1 | 10/2013 | Bennett et al. | |
| 2013/0304133 A1* | 11/2013 | Trauner | A61B 17/82 606/301 |
| 2014/0243829 A1* | 8/2014 | Cavallazzi | A61B 17/74 606/71 |
| 2014/0243837 A1* | 8/2014 | Mebarak | A61B 17/1728 606/96 |
| 2014/0243841 A1* | 8/2014 | Cavallazzi | A61B 17/8869 606/103 |
| 2014/0243901 A1* | 8/2014 | Mebarak | A61B 17/1728 606/281 |
| 2014/0243905 A1* | 8/2014 | Cavallazzi | A61B 17/746 606/286 |
| 2014/0243907 A1* | 8/2014 | Cavallazzi | A61B 17/74 606/286 |
| 2015/0297271 A1* | 10/2015 | Finley | A61B 17/8004 606/281 |

* cited by examiner

MEDICAL IMPLANT SYSTEM FOR SECURING BONE FRAGMENTS

BACKGROUND OF THE INVENTION

1. Field of the Invention

The present invention relates to a medical implant system for securing bone fragments, and, more particularly to a connector for use with a bone plate for securing bone fragments.

2. Description of the Related Art

The fracture of bones, whether it be due to impact or stress, or to certain medical conditions which weaken the bones, is generally treated by restoring the fractured pieces to their original positions and then immobilizing them to allow for the natural healing process of bone in-growth to fuse the bone fragments. Aligning the bone fragments, also known as reduction, is verified, for example, through X-rays of the affected area.

Depending upon the severity and position of the break, it is sometimes possible to immobilize the fragments externally, without surgery through the use of a plaster or fiberglass cast or splint. It may further be possible to immobilize the fragments using a specialized brace. If, however, surgery is required to re-align the bones into their natural position, alternative methods of immobilizing the bone fragments must be utilized.

It is known to utilize rigid plates in association with bone pins and/or bone screws to secure the bone fragments in position. Additional implants are known which utilize wires in coordination with rigid plates, for immobilization of bone fragments.

What is needed in the art is a system or device which provides for effective bone fragment fixation and provides a secure fixation, which even should the device slip or be slightly displaced from its original position, maintains sufficient tension to hold the device in position and maintain the immobility of the bone fragments.

SUMMARY OF THE INVENTION

The present invention provides a system for securing bone fragments securely in position with a dynamic connector having a tensioning mechanism.

The invention in one form is directed to a medical implant system for securing bone fragments in position. The medical implant system includes a bone plate including a groove, a dynamic connector positioned within said groove of said bone plate, and an elongate flexible member. The dynamic connector includes a tip end having a through-hole, a tension spring having an end coupled to the tip end, and a head coupled to an opposing end of the tension spring. The elongate flexible member extends through said through-hole of said tip end and is secured to the head.

The invention in another form is directed to a medical implant system including a bone plate having a groove, a dynamic connector positioned within the groove of the bone plate, and a flexible, elongate member. The dynamic connector includes a head having an attachment structure and an elongate body coupled with the head. The elongate body has a tip end and a resilient portion allowing stretching of the elongate body in a longitudinal direction. The flexible, elongate member is coupled with the attachment structure of the head and the tip end of the elongate body.

The invention in another form is directed to a method for securing bone fragments in position. The method includes the steps of providing a bone plate including a groove and positioning a connector within the groove of the bone plate. A flexible elongate member is positioned through a through-hole in a tip end of an elongate body of the connector. The bone plate is positioned in a predetermined position over the bone fragments, and the elongate flexible member is extended around the bone. The elongate flexible member is tensioned by way of a tension spring of the connector and secured to a head of the connector.

Advantageously the present invention provides a medical implant system for securing bone fragments in position which reduces the risk of slipping.

An advantage of the present invention is that even if the inventive system slips from its original position, the tension is not completely lost, but rather merely reduced slightly.

Another advantage is the inventive system is easier to insert into position than the larger crimped down instruments known from the prior art.

Yet another advantage is that with the inventive connector of the present invention, it is feasible to utilize a suture as the flexible member, which can be stronger than twisted cerclage cable known from the prior art.

Additionally, the inventive medical implant system according to the present invention minimizes the risk of breaking or snapping the dynamic connector in comparison to connectors of the prior art.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate one embodiment of the invention and such exemplification is not to be construed as limiting the scope of the invention in any manner.

DETAILED DESCRIPTION OF THE INVENTION

Figure 1:
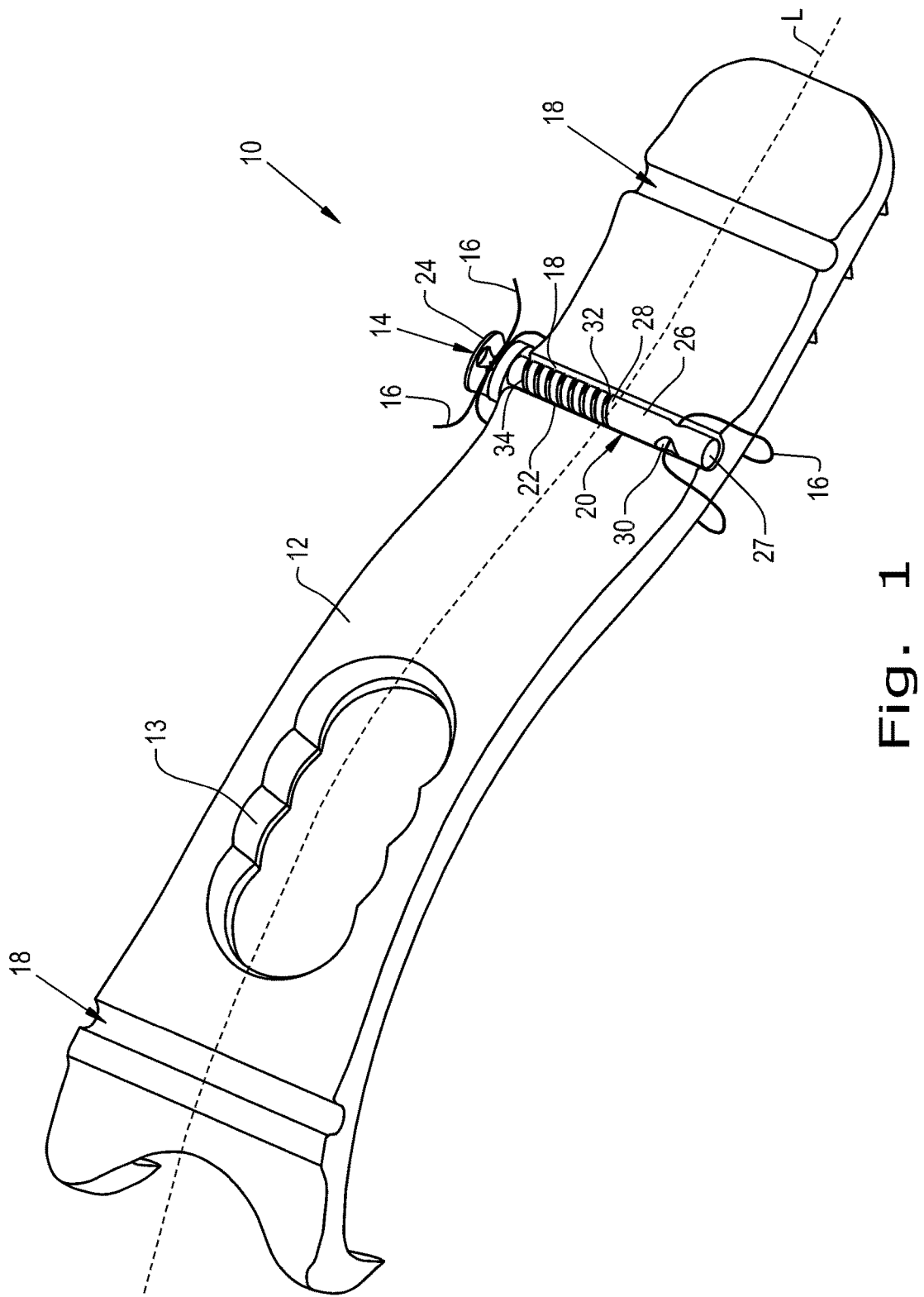
FIG. 1 is a perspective view of a medical implant system according to the present invention.

Referring now to the drawings, and more particularly to FIGS. 1-5, there is shown a medical implant system 10 which generally includes a bone plate 12, a dynamic connector 14 and an elongate, flexible member 16.

Bone plate 12 includes grooves 18, which are shown in FIGS. 1-5 as extending transverse to a longitudinal axis L of bone plate 12. It is, however, feasible for grooves 18 to extend parallel to longitudinal axis L of bone plate 12, dependent upon the application. Further, although the embodiment illustrated in FIGS. 1-5 is shown as having three grooves 18, any number of grooves 18, for example, 2, 3, 4 or more, may be present in bone plate 12 for receiving dynamic connectors 14. Bone plate 12 is illustrated in the present embodiment as having a complex s-shaped curvature. However, bone plate 12 may have a complex or simple curvature, or no curvature at all. For example, bone plate may be generally formed to fit around, for example, an elongate bone 20, such as a tibia, femur or humerus, or for example for use in association with a lateral hip plate. It is also feasible for bone plate 12 to be formed of a material with sufficient flexibility to be bent into a shape which fits securely against the surface of a bone. In addition, medical implant system 10 may be configured to be utilized in association with a proximal hip claw in order to fit, for example, over the end of a bone. Further, in the present embodiment, bone plate 12 is shown with a single, irregularly shaped through-hole feature 13. Through-hole feature 13 can be any number or combination of holes and slots in addition to grooves 18.

Bone plate 12 is formed of a biocompatible material, for example, a polymeric material a composite material or a metal. Exemplary polymeric materials which would be suitable for use include polyaryletherketone (PAEK), such as polyetheretherketone (PEEK). Exemplary biocompatible metals for use to form bone plate 12 include stainless steel, titanium and titanium alloys, such as titanium-aluminum-niobium, cobalt and cobalt alloys, such as cobalt-chrome or cobalt-chrome-molybdenum, and aluminum and aluminum alloys.

Figure 2:
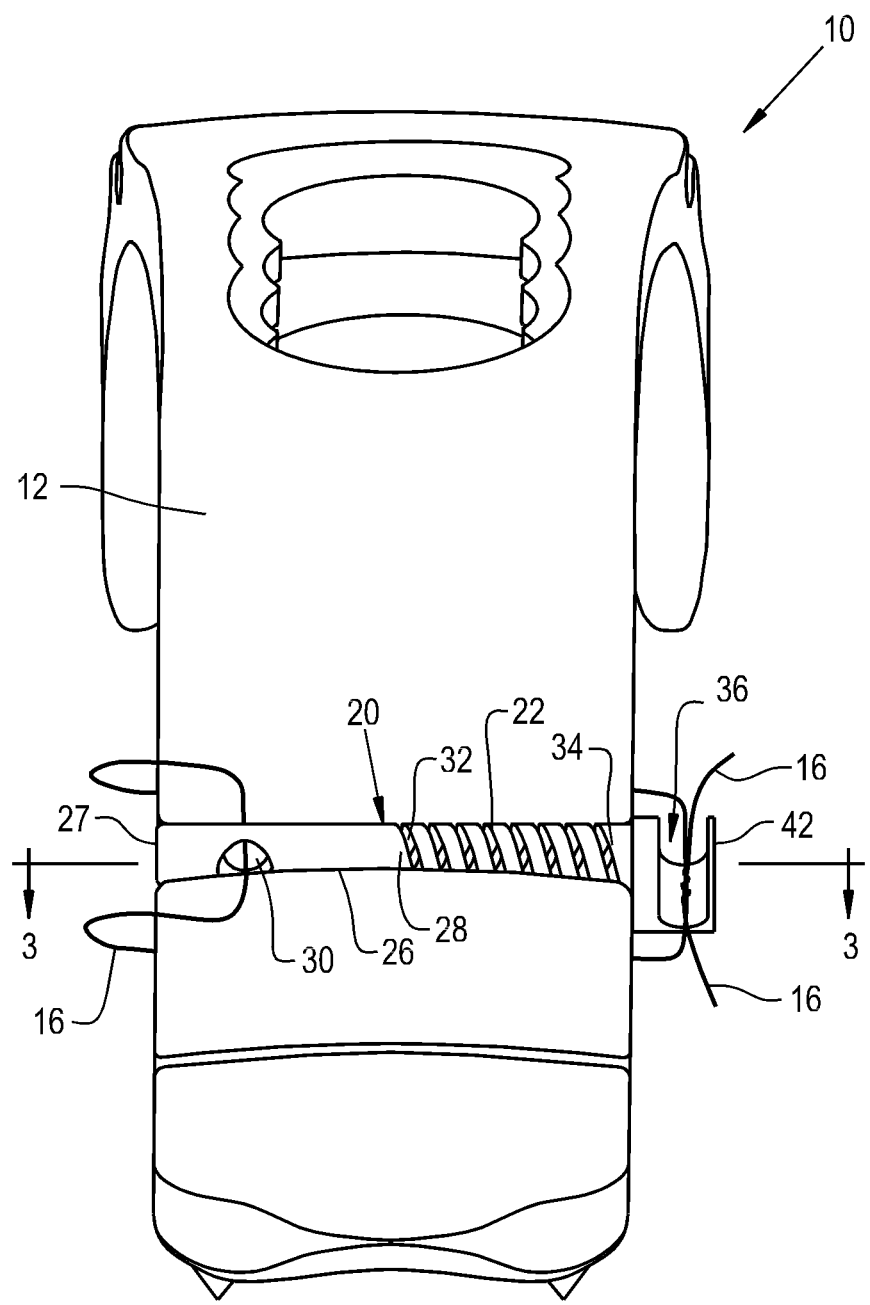
FIG. 2 is an end view of the medical implant system of FIG. 1.
Figure 3:
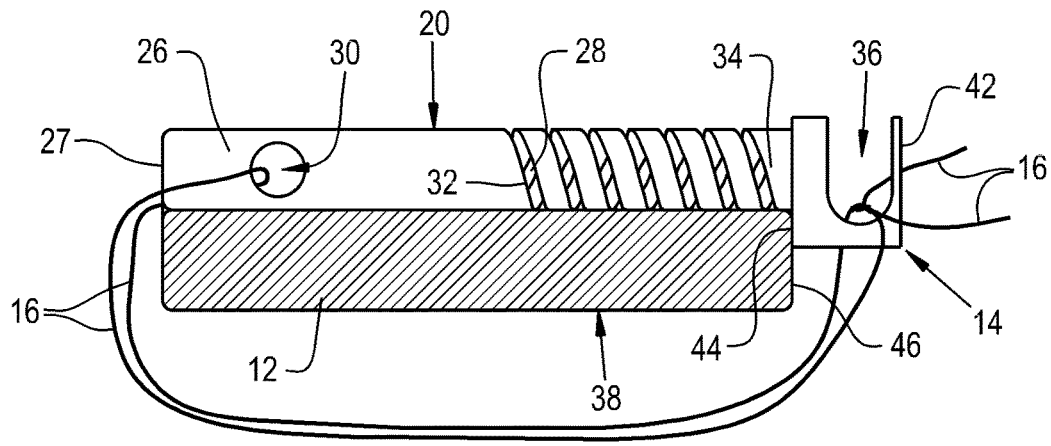
FIG. 3 is a sectional view of the medical implant system according to FIGS. 1 and 2, taken along line 3-3 in FIG. 2.

Dynamic connector 14 generally includes an elongate body 20 and a head 24, as illustrated in FIGS. 1-3. Elongate body 20 includes a resilient portion 22 and a tip end 26. Tip end 26 has a pair of opposing ends 27, 28 and a through-hole 30 extending through tip end 26. Elongate body 20 is sized and shaped to be received within groove 18, for example in the embodiment shown in the FIGS. 1-5, entirely within groove 18. Elongate body 20 is shown in the embodiment illustrated in FIGS. 1-5 as having a circular cross-section. However, the shape of the cross-section of elongate body 20 may, for example, be oval or polygonal, for example, triangular, square, rectangular, etc.

According to the embodiment shown in FIGS. 1-3, resilient portion 22 is in the form of a tension spring 22 having one end 32 coupled with end 28 of tip end 26 elongate body 20, while an opposing end 34 of tension spring 22 is coupled with head 24 of dynamic connector 14. It is, however, feasible for tension spring 22 to be positioned anywhere along the length of dynamic connector 14. For example, it is feasible for tension spring 22 to be positioned closer to tip end 26 of elongate body and for a second portion of elongate body 20 to be coupled with head 24. Tension spring 22 may be integrally coupled with elongate body 20 and/or head 24. Further, tension spring 22 may be positioned entirely within groove 18 such that no portion of the tension spring 22 extends above an edge of groove 18 of bone plate 12. In other words, tension spring 22 may be sized and shaped to be received entirely within groove 18. The same is true of elongate body 20. Elongate body 20 may be sized and shaped to be received entirely within groove 18. Although resilient portion 22 is a tension spring in the embodiment shown in FIGS. 1-3, it may be in the form of, for example, any resilient material, such as polymeric material.

Figure 4:
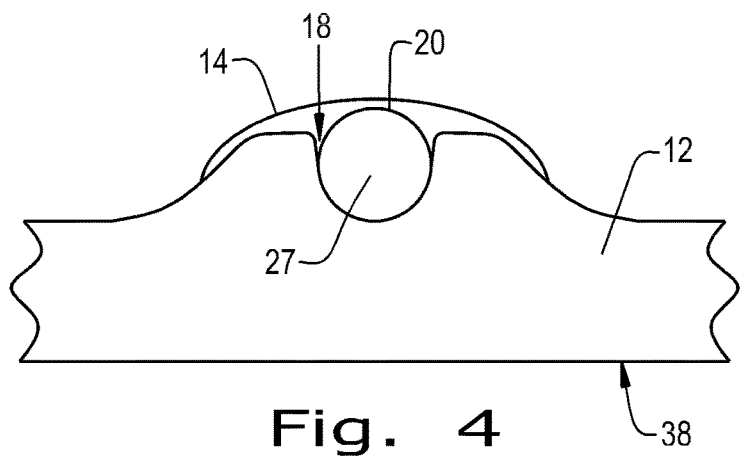
FIG. 4 is a fragmented side view of the medical implant system according to FIGS. 1-3, illustrating an end of the connector according to the present invention.
Figure 5:
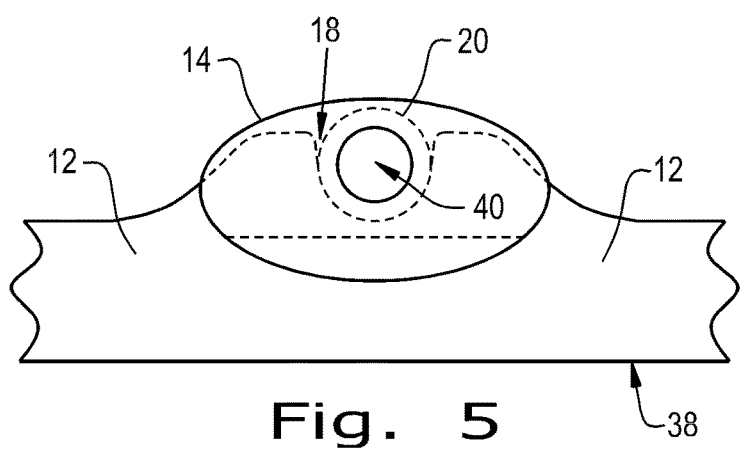
FIG. 5 is a fragmented side view of the medical implant system according to FIGS. 1-4, illustrating an opposite end of the connector according to the present invention.

Head 24 is formed such that elongate, flexible member 16 may be tied off around head 24, for example around groove 36. Groove 36 is in a location for access to twist down wire or tighten a self-locking adjustable loop construct to tie off the dynamic connector 14. For example, groove 36 is positioned such that it opens away from the bone onto which it is placed, or away from a bone-side surface 38 of bone plate 12, as illustrated in FIGS. 3-5. Head 24 includes at least one through-bore 40, for example two through-bores 40, extending through a wall 42 defining groove 38. The at least one through-bore 40 in head 24 transects groove 36 in head 24. Head 24 further includes a portion 44 of head 24 which abuts a side edge 46, further securing dynamic connector in position against bone plate 12.

Dynamic connector 14 is formed, at least in part, of a resilient biocompatible material, for example, a polymeric material, a composite material and a metal or metal alloy. The metal or metal alloy is, for example, titanium or a titanium alloy, such as titanium-aluminum-niobium, stainless steel, or cobalt or a cobalt alloy, such as cobalt chrome or cobalt-chromium-molybdenum. An exemplary biocompatible polymer material is a polyaryletherketone (PAEK), such as polyetheretherketone (PEEK).

The elongate, flexible member 16 can be, for example, a suture, a cable, a wire or self-locking adjustable loop construct formed of a biocompatible material, for example polyethylene and may be further secured with dynamic connector 14, for example, using a self-locking adjustable suture loop according to U.S. Pat. No. 7,601,165, which is incorporated herein by reference in its entirety.

The present invention further provides a method of securing bone fragments during a surgical procedure utilizing the inventive medical implant system. According to the inventive method, bone plate 12 is provided including groove 18, as illustrated in FIG. 1. Dynamic connector 14, which is, for example, sized and shaped to be received within groove 18 of bone plate 12, is positioned within the groove 18 of bone plate 12, as shown in FIGS. 1-5. A flexible, elongate member 16 is extended or positioned through through-hole 30 in tip end 26 of elongate body 20 of the dynamic connector 14, as illustrated in FIGS. 1-3. The bone plate 12 is positioned at a predetermined location over a plurality of pre-identified bone fragments. The bone plate may further be formed such that the shape of the bone plate corresponds to the shape of the bone over which it is being placed. The elongate, flexible member 16, for example at least one suture 16, is extended around the bone. The suture 16 is tensioned using the tension spring 22 of dynamic connector 14. The suture 16 is secured to the head 24 of the dynamic connector 14, for example, secured in the groove 36 of the head 24. It is also feasible for suture 16 to be secured through a through-bore 40 in the head 24 of the dynamic connector 14, thereby more securely fixing same into position. The tensioning step may be prior to and/or subsequent to securing suture 16 to the head 24 of dynamic connector 14. For example, the tension spring 22 can either stretch during tie off of the suture 16 or be pre-stretched by a tensioner (not shown) so that once everything is secure the tensioner can be removed and load the dynamic connector 14 even more.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A medical implant system for securing bone fragments in position, said implant system comprising:
   a bone plate including a groove;

a dynamic connector positioned within said groove of said bone plate, said dynamic connector including:
a tip end having a through-hole;
a tension spring having an end coupled to said tip end; and
a head coupled to an opposing end of said tension spring; and
an elongate flexible member extending through said through-hole of said tip end and secured to said head.

2. The medical implant system according to claim 1, said tension spring being integrally coupled with at least one of said elongate body and said head.

3. The medical implant system according to claim 2, said tension spring being positioned entirely within said groove of said bone plate.

4. The medical implant system according to claim 3, said tension spring being a spiral tension spring.

5. The medical implant system according to claim 1, said head including a groove extending parallel to a longitudinal axis of said bone plate when positioned in said groove of said bone plate and transverse to a longitudinal axis of said elongate body of said dynamic connector.

6. The medical implant system according to claim 5, said head having at least one through-bore extending through an end wall and transverse to said groove in said head.

7. The medical implant system according to claim 6, at least one through-bore transecting said groove in said head.

8. The medical implant system according to claim 7, said head including a portion abutting a side edge of said bone plate.

9. The medical implant system according to claim 1, said dynamic connector is formed at least in part from a resilient biocompatible material.

10. The medical implant system according to claim 9, said resilient biocompatible material being one of a polymer material, a composite material and a metal.

11. The medical implant system according to claim 10, wherein said metal is one of titanium, stainless steel, cobalt chrome, cobalt-chromium-molybdenum, and titanium-aluminum-niobium.

12. The medical implant according to claim 10, said polymer material being a polyaryletherketone (PAEK).

13. The medical implant according to claim 12, said PAEK being polyetheretherketone (PEEK).

14. The medical implant system according to claim 1, said flexible member being one of a cerclage cable, a wire, a suture and a self-locking adjustable loop construct.

15. A medical implant system, comprising:
a bone plate having a groove;
a dynamic connector positioned within said groove of said bone plate, said dynamic connector including:
a head having an attachment structure;
an elongate body coupled with said head, said elongate body having a tip end and
a resilient portion allowing stretching of said elongate body in a longitudinal direction; and
a flexible, elongate member coupled with said attachment structure of said head and said tip end of said elongate body.

16. The medical implant system according to claim 15, said resilient portion being a tension spring.

17. The medical implant system according to claim 16, said bone plate including a plurality of grooves and a corresponding plurality of dynamic connectors positioned within said grooves.

18. The medical implant system according to claim 15, said elongate body being integrally formed with said head.

19. A method for securing bone fragments in position, the method comprising the steps of:
providing a bone plate including a groove;
positioning a dynamic connector within said groove of said bone plate;
positioning a flexible elongate member through a through-hole in a tip end of an elongate body of said dynamic connector;
positioning said bone plate in a predetermined position over the bone fragments;
extending said elongate flexible member around the bone and securing said elongate flexible member to an opposite end of said dynamic connector such that tension is applied to said elongate flexible member;
tensioning said elongate flexible member by way of a tension spring of said dynamic connector; and
securing said elongate flexible member to a head of said dynamic connector.

20. The method according to claim 19, further comprising the step of preloading said tension spring prior to said tensioning step.

21. The method according to claim 19, said tension spring being integrally formed with at least one of said elongate body and said head of said dynamic connector.

* * * * *